United States Patent
Job

(10) Patent No.: US 6,759,362 B2
(45) Date of Patent: Jul. 6, 2004

(54) MIXED METAL ALKOXIDE COMPLEXES AND POLYMERIZATION CATALYSTS MADE THEREFROM

(75) Inventor: Robert Charles Job, Bound Brook, NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 92 days.

(21) Appl. No.: 10/141,739

(22) Filed: May 8, 2002

(65) Prior Publication Data

US 2003/0050184 A1 Mar. 13, 2003

Related U.S. Application Data

(62) Division of application No. 09/395,917, filed on Sep. 14, 1999, now abandoned.
(60) Provisional application No. 60/141,629, filed on Jun. 30, 1999.

(51) Int. Cl.[7] .............................. C08F 4/02; C08F 4/60; B01J 31/00; B01J 37/00
(52) U.S. Cl. ...................... 502/113; 302/129; 302/133; 302/169; 302/171
(58) Field of Search ................................ 502/113, 129, 502/133, 169, 171

(56) References Cited

U.S. PATENT DOCUMENTS

| | | | |
|---|---|---|---|
| 3,901,863 A | 8/1975 | Berger et al. ........... 260/88.2 R |
| 4,109,071 A | 8/1978 | Berger et al. ................ 526/114 |
| 4,456,695 A | 6/1984 | Nimura et al. .............. 502/104 |
| 4,518,751 A | 5/1985 | Mizogami et al. .......... 526/114 |
| 4,525,468 A | 6/1985 | Mack et al. ................. 502/104 |
| 4,870,040 A | 9/1989 | Job ............................. 502/104 |
| 5,106,806 A * | 4/1992 | Job ............................. 502/111 |
| 5,124,298 A | 6/1992 | Job ............................. 502/127 |
| 6,399,531 B1 * | 6/2002 | Job et al. ..................... 502/104 |
| 6,444,605 B1 * | 9/2002 | Job et al. ..................... 502/113 |
| 2001/0051697 A1 * | 12/2001 | Morse ......................... 526/119 |
| 2002/0016255 A1 * | 2/2002 | Job ............................. 502/113 |
| 2002/0037979 A1 * | 3/2002 | Job et al. ..................... 528/110 |

FOREIGN PATENT DOCUMENTS

| | | |
|---|---|---|
| DE | 3004650 | 8/1981 |
| EP | 43473 | 1/1982 |
| EP | 273208 | 11/1987 |
| EP | 294168 | 11/1991 |
| EP | 602508 | 6/1994 |
| EP | 607773 | 7/1994 |
| JP | 55040745 | 3/1980 |
| JP | 58047003 | 9/1981 |
| JP | 3124710 | 10/1989 |
| JP | 2145609 | 6/1990 |
| JP | 6016718 | 1/1994 |
| JP | 7062016 | 3/1995 |
| JP | 63069806 | 8/1995 |
| WO | 9403508 | 2/1994 |
| WO | 9415977 | 7/1994 |
| WO | 9720790 | 6/1997 |

\* cited by examiner

Primary Examiner—Mark L. Bell
Assistant Examiner—J. Pasterczyk

(57) ABSTRACT

A process for making a solid composition comprising alkoxide groups, chloride groups, one or more metals, M, in the +2 oxidation state selected from Mg, Ca, Mn, Cu, Co or Zn, and one or more metals, T, in the +3, +4 or +5 oxidation state selected from Ti, Zr, V, Sm, Fe, Ni, Rh, Co, Cr, Mo, W or Hf, the molar ratio M/T of the composition being from 2.5 to 3.75, said process comprising contacting one or more alkoxide containing compounds of metal M, one or more alkoxide compounds of metal T, and a halide compound, the molar ratio M/T of the contacting compounds being from 2.5 to 3.5, and recovering the resulting solid.

8 Claims, No Drawings

MIXED METAL ALKOXIDE COMPLEXES AND POLYMERIZATION CATALYSTS MADE THEREFROM

This is a division of applicants' prior copending application, Ser. No. 09/395,917, filed Sept. 14, 1999, now abandoned. Which claims the benefit of Provisional application No. 60/141,629 filed Jun. 30, 1999.

BACKGROUND OF THE INVENTION

1. Field of the Invention

The present invention relates to mixed metal alkoxide complexes useful as precursors for polymerization procatalysts that are ultimately useful in polymerizing α-olefins. The precursor complexes can be prepared by reacting a mixture of various metal alkoxides, halides or amides in the presence of a clipping agent to form a solid complex. The solid complex then can be used to form a procatalyst by contacting it with a halogenating agent and optionally an electron donor. The procatalyst then can be converted to an olefin polymerization catalyst by contacting it with a cocatalyst and optionally a selectivity control agent

2. Description of Related Art

Polymers and copolymers of lower α-olefins, particularly, ethylene, propylene and butylene are widely used throughout the world. These polymeric products are relatively inexpensive to manufacture, and they exhibit a number of commercially useful properties. These polymers are most commonly utilized in the form of highly crystalline solids. During the polymerization process, whether it be by liquid pool, gas phase, slurry phase or any other commonly utilized process, it is beneficial for the polymer particles (and consequently the catalyst particles) to be of a satisfactory shape and size. As examples: denser particles allow for higher hourly production rates; spheroidal particles allow for higher polymer bulk density; narrow particle size distribution allows for better gas phase fluidization. Overly small catalyst and polymer particles (commonly called fines) are also undesirable.

When ethylene is polymerized, the process is less complicated than with higher olefins in that the product type is not greatly influenced by the manner in which the ethylene molecules add to the growing polymeric chain during polymerization. The polymeric product of ethylene does not generally exist in stereoisomeric forms. The simpler catalysts required to effect this polymerization can normally be obtained by straightforward chlorination of a catalyst precursor. If the shape of the catalyst particle and thus the shape of the resulting polymer particle is of importance, the catalyst precursor must be sufficiently robust so that it can withstand the rigors of this chlorination step.

When propylene is polymerized, however, the presence of pendant methyl groups on the polymeric chain provides a possibility of several product types, depending on the steric regularity with which propylene molecules add to the growing chain. Much if not most of the commercial polypropylene results from the stereoregular addition of propylene molecules in a regular head-to-tail manner. The form of polymer having a substantial proportion of random addition of propylene units is termed atactic and this amorphous form is less desirable. If present in a significant proportion, the atactic polymer must be removed through an extraction process to provide a more desirable crystalline material.

These polymers typically are formed by using a polymerization catalyst. The activity of the catalyst is significant in that the more polymer produced per unit weight of catalyst the better. The early titanium, chromium or vanadium catalysts were of low activity and the product contained a significant proportion of catalyst residues. These residues had to be removed in an effort to obtain commercially satisfactory properties.

More recent titanium-based olefin polymerization catalysts are stereoregulating and have sufficient activity to avoid extraction and deashing. These high activity catalysts typically are prepared via chlorination of a magnesium containing precursor, in the presence of an electron donor compound, to form a solid procatalyst that usually contains magnesium, titanium and halide moieties, and comprises additionally a cocatalyst (usually an organoaluminum compound) and an optional selectivity control agent (SCA) for propylene polymerization. The magnesium containing complex is typically referred to as a "precursor", the solid titanium-containing compound typically is referred to as a "procatalyst", the organoaluminum compound, whether complexed or not, usually is referred to as the "cocatalyst" and the third component external electron donor, whether used separately or partially or totally complexed with the organoaluminum compound, is referred to as the "selectivity control agent." Throughout this disclosure, these terms will be used in accordance with the aforementioned designations. As before, if the shape of the catalyst particle and thus the shape of the resulting polymer particle is of importance, the catalyst precursor must be sufficiently robust so that it can withstand the rigors of the chlorination process.

Many chemical combinations of procatalysts, cocatalysts and selectivity control agents are known in the art to produce active catalysts. Through considerable experience, however, certain materials are of greater interest than others. For example, there is significant research in the area of procatalysts, which typically contain some chemical combination of magnesium, titanium tetrachloride and an internal electron donor. These internal electron donors usually are oxygen containing compounds such as tetrahydrofuran and aromatic esters such as ethyl benzoate or ethyl p-toluate. Conventional cocatalysts include an aluminum trialkyl such as triethylaluminum or triisobutylaluminum that is often complexed with a portion of the selectivity control agent (or external electron donor), which also is typically an aromatic ester or an organosilane. Although variations in any of these catalyst components will influence the performance of the resultant catalyst, the component that appears to offer the greatest opportunity for modification to produce greater catalyst activity is the procatalyst.

The literature is rife with disclosures relating to the various known methods of preparing procatalysts. For example, Kioka, et al., U.S. Pat. No. 4,330,649, the disclosure of which is incorporated by reference herein in its entirety, describes a solid catalyst component (procatalyst) that is prepared by heating a soluble magnesium compound such as magnesium chloride with a higher alcohol in the presence of an ester to produce a solution. This solution contains a "precursor" of the procatalyst, which then is added to titanium tetrachloride and an electron donor (internal) to form the procatalyst. A number of United States patents issued to Robert C. Job (and Robert C. Job, et al.,) describe various mechanisms for preparing magnesium-containing, titanium-containing compounds that are useful as precursors for the production of procatalysts that are ultimately useful in preparing catalysts for the polymerization of α-olefins. For example, U.S. Pat. Nos. 5,034,361; 5,082,907; 5,151,399; 5,229,342; 5,106,806; 5,146,028; 5,066,737; 5,122,494, 5,124,298, and 5,077,357, the disclosures of which are incorporated by reference herein in their entirety, disclose various procatalyst precursors. U.S. Pat. No. 5,034,361 discloses solubilizing a magnesium alkoxide in an alkanol solvent by interaction of the magnesium alkoxide compound and certain acidic materials. This magnesium alkoxide then can be used either directly as a magnesium-containing catalyst precursor, or can be reacted with various titanium compounds to produce a magnesium and titanium-containing catalysts precursor.

U.S. Pat. Nos. 5,082,907; 5,151,399; 5,229,342; 5,106,806; 5,146,028; 5,066,737; 5,122,494, 5,124,298, and 5,077,357 disclose various magnesium and titanium-containing catalyst precursors, some of which are prepared by using the aforementioned magnesium alkoxide as a starting material. These precursors are not active polymerization catalysts, and they do not contain any effective amounts of electron donor. Rather, the precursors are used as starting materials in a subsequent conversion to an active procatalyst. Magnesium and titanium-containing procatalysts are formed by chlorinating the magnesium and titanium-containing precursor with a tetravalent titanium halide, an optional hydrocarbon and an optional electron donor. The resulting procatalyst solid then is separated from the reaction slurry (by filtration, precipitation, crystallization, and the like). These procatalysts then are converted to polymerization catalysts by reaction with, for example, an organoaluminum compound and a selectivity control agent.

While these magnesium and titanium-containing procatalysts are very effective in producing polyolefins, they are not as effective in producing polyolefins with unconventional properties. For example, these traditional Ziegler-Natta procatalysts typically are not used, in conjunction with other catalysts (i.e., metallocenes), to make polymers having a bimodal molecular weight distribution. The magnesium and titanium-containing procatalysts known in the art also are not prepared to have specifically tailored catalyst decay rates, which is a useful attribute in assuring homogeneous product composition over a range of reactor residence times, and is a useful attribute when the catalyst is used in consecutive reactor polyolefin processes. In addition, these procatalysts are sensitive to esoteric, or unconventional comonomers, like dienes and the like, and they typically lose a substantial portion of their activity in the presence of such comonomers.

SUMMARY OF THE INVENTION

There exists a need to develop a procatalyst precursor that can be converted to an olefin polymerization catalyst capable of producing polymers in high yield, low fines, improved average particle size and increased bulk density. There also exists a need to provide a method of making a substantially spheroidal procatalyst having controlled catalyst decay rates, and a method of making a substantially spheroidal procatalyst capable of making tailored polymer particles having desired molecular weight distributions (narrow, broad, dissimilar, etc.). In addition, there exists a need to develop a precursor that can be converted into a polymerization catalyst that is not severely poisoned by esoteric olefin comonomers, and which has excellent activity. A need also exists to develop a precursor and method of making a precursor that does not suffer from any of the aforementioned disadvantages.

In accordance with these and other features of the invention, there is provided a mixed metal complex precursor containing, as the mixed metal portion, $(M1M2)_x(T1T2)_y$ where M1 and M2 may be the same or different and are selected from one or more metals having a +2 oxidation state, T1 and T2 may be the same or different and are selected from one or more metals having oxidation states of +3, +4 and +5, and wherein the molar ratio of x/y is about 2.5 to 3.75, with the proviso that if M1 and M2 are both Mg then T1 and T2 cannot both be chosen from Zr and $Ti^{+4}$. The precursor also has, complexed to the mixed metal portion, at least one group selected from alkoxide groups, phenoxide groups, halides, hydroxy groups, carboxyl groups and amide groups. The invention also provides a method of making the precursor comprising contacting a mixture of M1 and M2 metal alkoxides, halides, carboxyls, amides, phenoxides or hydroxides with a mixture of T1 and T2 metal alkoxides, halides, carboxyls, amides, phenoxides or hydroxides to form a solid precursor complex, and then separating the solid complex from the mixture. In accordance with this method, a clipping agent preferably is used and, optionally, a halide and an aliphatic alcohol can be used to form the solid precursor complex.

In accordance with another feature of the invention, there is provided a procatalyst prepared by reacting the above-mentioned precursor with an appropriate halogenating agent, and optional electron donor, where the procatalyst, when converted to a catalyst and used to polymerize at least one olefin, has improved catalytic activity and yields polymer having a broad molecular weight distribution, excellent bulk density, melt index, flow index and melt flow rate. In addition, the catalyst has a controlled catalyst decay rate.

The invention also provides a high activity olefin polymerization procatalyst that comprises: (i) the procatalyst precursor comprising the mixed metal portion as described above; (ii) an electron donor; (iii) a halide of tetravalent titanium; and (iv) optionally, a hydrocarbon. The invention additionally provides a high activity olefin polymerization catalyst that comprises: (i) the above-described procatalyst; (ii) an organoaluminum cocatalyst; and (iii) an optional selectivity control agent. The invention also provides methods of making each of the above-described precursors, procatalysts and catalysts. In addition, the invention provides methods of polymerizing olefins (homopolymers, copolymers, terpolymers, etc.) by contacting an olefin monomer (or monomers) with the above-described high activity olefin polymerization catalyst.

These and other features of the present invention will be readily apparent to those skilled in the art upon reading the detailed description that follows.

DESCRIPTION OF PREFERRED EMBODIMENTS

Throughout this description, the expression "clipping agent" denotes a species that is capable of assisting in the breakup of a polymeric magnesium alkoxide. Specifically, clipping agents include: (i) those species which, in large excess are capable of dissolving magnesium alkoxides; (ii) large anions; and (iii) those that prevent magnesium alkoxides from polymerizing.

Throughout this description the term "precursor" and the expression "procatalyst precursor" denotes a solid material that contains a mixture of M1, M2, T1, and T2 metals, (keeping in mind that M1, M2, T1, and T2 each can comprise more than one metal), but does not contain an electron donor, and which can be converted to a "procatalyst" (defined below) by contacting it with a halogenating agent such as alkylaluminum halide or tetravalent titanium halide (preferably $TiCl_4$) and optionally an electron donor. Throughout this description, the term "procatalyst" denotes a solid material that is an active catalyst component, and that can be converted to a polymerization catalyst by contact with an organoaluminum compound (preferably triethyl aluminum (TEAL) and aluminoxane), and an optional external donor, or selectivity control agent.

The present invention relates to a mixed metal alkoxide complex precursor containing, as the mixed metal portion, $(M1M2)_x(T1T2)_y$ where M1 and M2 may be the same or different and are selected from one or more metals having a +2 oxidation state, T1 and T2 may be the same or different and are selected from one or more metals having oxidation states of +3, +4 and +5, and wherein the molar ratio of x/y is from about 2.5 to about 3.75, with the proviso that if M1 and M2 are both Mg, then T1 and T2 cannot both be chosen from Zr and $Ti^{+4}$. The precursor also has, complexed to the mixed metal portion, at least one group selected from alkoxide groups, phenoxide groups, halides, hydroxy groups, carboxyl groups and amide groups.

It is preferred in the present invention that M1 and M2 are one or more metals selected from the group consisting of Mg, Ca, Mn, Cu, Co and Zn, and mixtures thereof, and more preferably M1 and M2 are selected from Mg, Mn, and Co. Most preferably, M1 and M2 are the same and are Mg. It also is preferred in the present invention that T1 and T2 are one or more metals selected from the group consisting of Ti ($Ti^{+3}$ and $Ti^{+4}$), Zr, V ($V^{+4}$ and $V^{+5}$), Sm, Fe, Sn, Ni, Rh, Co, Cr., Mo, W and Hf, and mixtures thereof, more preferably T1 and T2 are selected from Ti and Zr. In addition, the mixture of T1 and T2 preferably is not a mixture of titanium and zirconium.

The molar ratio of the M1 and M2 metals to the T1 and T2 metals, (i.e., the ratio of x/y) preferably is within the range of from 2.5 to 3.75, more preferably within the range of from 2.7 to 3.5 and most preferably, the molar ratio is 3. The mixed metal alkoxide precursor also has, complexed to the mixed metal portion, at least one group selected from alkoxide groups, phenoxide groups, halides, hydroxy groups, carboxyl groups and amide groups. Preferably, alkoxide groups and halide groups are complexed to the mixed metal portion to form the mixed metal alkoxide precursor of the present invention.

The mixed metal alkoxide precursor can be made by any method capable of forming a complex between the mixture of metals, and the additional complexing groups, at least one of which is selected from alkoxide groups, phenoxide groups, halides, hydroxy groups, carboxyl groups and amide groups. Preferably, the precursor is prepared by contacting a mixture of M1 and M2 metal alkoxides, halides, carboxyls, amides, phenoxides or hydroxides with a mixture of T1 and T2 metal alkoxides, halides, carboxyls, amides, phenoxides or hydroxides to form a solid precursor complex, and then separating the solid complex from the mixture. In accordance with this method, a clipping agent preferably is used and, optionally, an aliphatic alcohol can be used to form the solid precursor complex. In addition, a halide can be used during the preparation of the mixed metal alkoxide precursor complex, preferably a chloride, and most preferably, $TiCl_4$.

A particularly preferred method of making the mixed metal alkoxide precursor of the invention is shown in the table below.

| | |
|---|---|
| {aM1 $(OR)_2$ + | a + b + c + i + j + k = 3; p + q = 2; |
| bM1Cl$_2$ + cM1XpYq | R, R', R" = alkyl having 1 to 10 carbon |
| iM2 $(OR)_2$ + jM2Cl$_2$ + | atoms, or mixtures thereof; |
| kM2XpYq} | X = halide or alkoxide; M1, M2 are +2 |
| | -continued |
| + | metal ions |
| | Y = halide or alkoxide or clipper anion |
| {dT1(OR')$_4$ + eT1Cl$_4$ + | 0.4 < d + e + f < 2; T1, T2 are +3, +4 |
| fT1Z$_4$ | or +5 metal ions; |
| 1T2(OR')$_4$ + mT2Cl$_4$ + | 0.8 < d + e + f + l + m + n < 1.2 is |
| n T2Z$_4$} | preferred; |
| + | Z = halide, alkoxide, amide or mixture; |
| gClipping agent | Clipping agent; |
| + | 0 < g ≦ 2; if Y is clipper then 0 < g + cq + kq < 2; |
| | 0.1 < g < 0.4 is preferred; |
| hR"OH | R"OH is an alcohol or mixtures thereof; and |
| | 0.5 < h < 8. |

Any clipping agent that is capable of carrying out the functions described above can be used in the present invention. Clipping agents useful in the present invention include species which in large amounts will dissolve the magnesium alkoxide, large anions, and species that prevent the magnesium alkoxide from polymerizing. Preferably, the clipping agents are selected from cresol, 3-methoxyphenol, 4-dimethylaminophenol, 2,6-di-tert-butyl-4-methylphenol or p-chlorophenol, HCHO, $CO_2$, $B(OEt)_3$, $SO_2$, $Al(OEt)_3$, $CO_3^=$, $Br^-$, $(O_2COEt)^-$, $Si(OR)_4$, $R'Si(OR)_3$, and $P(OR)_3$. In the above compounds, R and R' represent hydrocarbon groups, preferably alkyl groups, containing from 1–10 carbon atoms, and preferably R and R' are the same or different and are methyl or ethyl. Other agents that release large anions or form large anions in situ (i.e., clipping agent precursors) can be used, such as $MgBr_2$, carbonized magnesium ethoxide (magnesium ethyl carbonate), calcium carbonate, and the like. Thus, the expression "clipper anion" mentioned in the table above denotes these anions.

The clipping agent preferably is used in an amount less than that required to fully dissolve the magnesium alkoxide. Preferably, the clipping agent is used in an amount ranging from 0 (if a clipping agent precursor is used) to 0.67 moles of clipping agent for every mole of the mixture of M1 and M2. More preferably, the clipping agent is used in an amount ranging from about 0.01 moles to about 0.3 moles, and most preferably, from about 0.03 moles to about 0.15 moles per mole of the mixture of M1 and M2.

Any alcohol or mixtures of alcohols can be used to prepare the mixed metal alkoxide complex precursor. Preferably, the alcohol is an aliphatic alcohol, and more preferably, the alcohol is selected from methanol, ethanol, butanol, propanol, i-propyl alcohol, n-butyl alcohol, n-propyl alcohol, and mixtures thereof Most preferably the alcohol is ethanol, butanol, and mixtures thereof.

The mixed metal alkoxide complex precursor can be produced by any of the methods described in U.S. Pat. Nos. 5,122,494, 5,124,298, and 5,371,157, the disclosures of which are incorporated by reference herein in their entirety, including the modification of substituting the magnesium alkoxide and titanium tetraalkoxide with suitable mixed metal compounds (i.e., halides, alkoxides, amides, etc. of M1, M2, T1, and T2). The complex mixed metal-containing alkoxide compound preferably can be produced by reacting one or more M1 and M2 alkoxides, one or more T1 or T2 alkoxides, a halide selected from $TiCl_3$ $TiCl_4$, $VCl_4$, $FeCl_3$, $SnCl_4$, $HfCl_4$, $MnCl_2$, $MgCl_2$, and $SmCl_3$, and an optional phenolic compound in the presence of an inert reaction diluent. The diluent then can be removed to produce, as a particulate solid, the complex alkoxide compound. This solid then can be treated with a halogenating agent to produce an olefin polymerization procatalyst, which then can be used, in the optional presence of selectivity control agent, to promote the polymerization of lower α-olefins by polymerization techniques which are largely conventional.

The alkoxide moieties of the mixed metal alkoxides of M1 and M2 are the same as or are different from the alkoxide moieties of the mixed metal alkoxides of T1 and T2, it being understood that not all M1, M2, T1, and T2 metals are in the form of an alkoxide. Moreover, the alkoxide moieties of one metal alkoxide reactant can be the same as or different from the alkoxide moieties of the other metal alkoxide reactant. In part for reasons of complex alkoxide purity, it is preferred that all alkoxide moieties of the mixed metal alkoxides be the same. The preferred alkoxide moieties are methoxide or ethoxide (R and R' above are methyl or ethyl) and particularly preferred is ethoxide. Magnesium ethoxide, titanium tetraethoxide, zirconium tetraethoxide, and hafnium tetraethoxide are the preferred metal alkoxide reactants for the production of the mixed metal alkoxide complex.

If a phenolic compound is used to form the mixed metal alkoxide precursor, the phenolic compound preferably is selected from phenol or an activated phenol. By the term "activated phenol" is meant a monohydroxylic phenol of one aromatic ring having aromatic ring substituents other than hydrogen which serve to alter the pKa of the phenolic compound. Such substituent groups are free from active hydrogen atoms and include halogen, e.g., chlorine or bromine, alkyl and particularly alkyl of up to 4 carbon atoms inclusive, and dialkylamino wherein each alkyl has up to 4 carbon atoms inclusive. Suitable substituent groups do not include hydroxy. Illustrative of suitable phenolic compounds are phenol, p-cresol, o-cresol, 3-methoxyphenol, salicyl aldehyde, methyl salicylate, 2,6-di-t-butyl-4-methylphenol (BHT), 2,4-diethylphenol, p-chlorophenol, p-bromophenol, 2,4-dichlorophenol, p-dimethylaminophenol and m-diethylaminophenol.

The contacting of the mixed metal compounds, clipping agent (or clipper), optional halide, optional phenolic compound, and optional alcohol preferably takes place at an elevated temperature in an inert reaction diluent. The reaction diluent is one in which all reactants are at least partially soluble and which does not react with the reactants or the complex alkoxide product. Preferred reaction diluents are hydrocarbon such as isooctane, isopentane or n-heptane, or are halohydrocarbon such as methylene chloride, carbon tetrachloride or chlorobenzene. The contacting preferably takes place at a reaction temperature from about 50° C. to about 120° C. Contacting typically is effected in a suitable reactor and is facilitated by conventional procedures such as shaking, stirring or refluxing. The phenolic compound, if used, preferably is provided in a quantity of from about 0.01 mole to about 2 moles per mole of mixed T1 and T2 metals (e.g., titanium tetraalkoxide, titanium tetrachloride, vanadium tetrachloride and the like), but preferably in a quantity of from about 0.1 mole to about 0.4 moles per mole of mixed T1 and T2 metals. The mixed M1 and M2 metal compounds can be provided in a quantity from about 1.5 mole to about 8 moles per mole of mixed T1 and T2 metals. Preferred quantities of mixed M1 and M2 compounds are from about 2.5 moles to about 3.5 moles per mole of mixed T1 and T2 metals.

Upon contacting all of the components, the mixture then can be heated to anywhere from about 50° C. to about 120° C. by any suitable heating apparatus. The components are mixed at this elevated temperature for about 5 minutes to about 9 hours, preferably, from about 25 minutes to 7 hours, and most preferably from about 45 minutes to 2 hours; such time to be determined by visually inspecting the components for evidence of the consumption of original solid reactants. Those skilled in the art are capable of determining when the original mixed metal reactants have disappeared and/or when a homogeneous slurry has been formed, using the guidelines provided herein.

Upon forming the homogeneous slurry, the alcohol then is preferably removed from the solution by heating the solution at temperatures above 100° C., and/or passing nitrogen over the solution. Removal of alcohol enables the precipitation of additional mixed metal alkoxide complex which may remain dissolved in solution (i.e., solid precursor material) and results in enhanced yield of product. The solid complex then can be removed from the reaction mixture by conventional means.

Preferably, the solid precursor materials are separated from the reaction mixture by any suitable means, including but not limited to, decantation, filtration, centrifugation, and the like. More preferably, the solid material is filtered, most preferably under the impetus of pressure and/or temperature. The filtered solids then can be washed at least once with one or more solvents, including but not limited to monochlorobenzene, toluene, xylene, isopentane, isooctane, and the like. After separation from the mixture, (or mother liquor, and subsequent wash solvents), the solid procatalyst precursor preferably is dried. Drying typically is conducted by supplying dry, moisture-free inlet nitrogen at a temperature of about 25° C. to about 45° C. for anywhere from about 10 minutes to about 10 hours thereby resulting in a product that is substantially dry. Higher temperatures on the order of 50 to about 150° C. can be used to dry the precursor in shorter periods of time.

Any mechanism can be used to carry out the drying of the present invention. For example, the filter cake could be dried by flowing a heated inert gas stream through the cake for the time period described above. Alternatively, the filter cake could be removed from the filter and then subsequently dried in a conventional drying apparatus using direct, indirect, infrared, radiant or dielectric heat. Any apparatus capable of drying solids at temperatures above about 25° can be used in accordance with the present invention. Particularly preferred drying apparatus include, but are not limited to, direct continuous dryers, continuous sheeting dryers, pneumatic conveying dryers, rotary dryers, spray dryers, through-circulation dryers, tunnel dryers, fluid bed dryers, batch through-circulation dryers, tray and compartment dryers, cylinder dryers, screw-conveyor dryers, drum dryers, steam-tube rotary dryers, vibrating-tray dryers, agitated pan dryers, freeze dryers, vacuum rotary dryers and vacuum-tray dryers. Most preferably, the solid precursor material is dried in a single or multiple-leaf combined filter and dryer. Those skilled in the art are capable of designing a suitable dryer and drying protocol to effect drying the precursor in accordance with the present invention.

The precursor of the present invention then can be immediately converted to a procatalyst by any suitable means known to the art described below, or it can be stored for later use or for shipment to a facility capable of converting the precursor to a procatalyst. Upon drying, the solid precursor material can be discharged by any suitable means to downstream processing.

Conversion of the dried procatalyst precursor to a procatalyst can be accomplished in any suitable manner. For example, the dried precursors of the invention can be converted to polymerization procatalyst by reaction with a halide, like tetravalent titanium halide, an optional hydrocarbon or halohydrocarbon and an electron donor. The tetravalent titanium halide is suitably an aryloxy- or alkoxy di- or trihalide such as diethoxytitanium dichloride, dihexyloxytitanium dibromide or diisopropoxytitaniumchloride or the tetravalent titanium halide is a titanium tetrahalide such as titanium tetrachloride or titanium tetrabromide. A titanium tetrahalide is preferred as the tetravalent titanium halide and particularly preferred is titanium tetrachloride. Halogenation also can be carried out by any of several means known to the art. These include but are not limited to treatment of the precursor with $SiCl_4$, $R_xAlCl_{3-x}$, $BCl_3$ and the like. Suitable procatalyst preparation procedures are described in the aforementioned patents U.S. Pat. Nos. 5,124,298 and 5,132,263.

Any electron donor can be used in the present invention so long as it is capable of converting the precursor into a procatalyst. Suitable electron donors are those electron donors free from active hydrogens that are conventionally employed in the formation of titanium-based procatalysts. Particularly preferred electron donors include ethers, esters, amides, imines, nitriles, phosphines, stibines, dialkyoxy benzenes, and arsines. The more preferred electron donors, however, include esters and ethers, particularly alkyl esters of aromatic monocarboxylic or dicarboxylic acids and particularly aliphatic or cyclic ethers. Examples of such electron donors are methyl benzoate, ethyl benzoate, ethyl p-ethoxybenzoate, 1,2-dialkyoxy benzenes, ethyl p-methylbenzoate, diethyl phthalate, dimethyl naphthalene dicarboxylate, diisobutyl phthalate, diisopropyl terephthalate, diethyl eher and tetrahydrofuran. The electron donor is a single compound or is a mixture of compounds but preferably the electron donor is a single compound. Of the preferred electron donors, ethyl benzoate, 1,2-dialkoxy benzenes and diisobutyl phthalate are particularly preferred.

In a preferred embodiment, the mixture of procatalyst precursor, halide, electron donor and halohydrocarbon is maintained at an elevated temperature, for example, a temperature of up to about 150° C. Best results are obtained if the materials are contacted initially at or about ambient temperature and then heated. Sufficient halide is provided to convert at least a portion and preferably at least a substantial portion of the alkoxide moieties of the procatalyst precursor to halide groups. This replacement is conducted in one or more contacting operations, each of which is conducted over a period of time ranging from a few minutes to a few hours and it is preferred to have halohydrocarbon present during each contacting. Sufficient electron donor usually is provided so that the molar ratio of electron donor to the mixed metals (M1 and M2) present in the solid procatalyst is from about 0.01:1 to about 1:1, preferably from about 0.05:1 to about 0.5:1. The final washing with light hydrocarbon produces a procatalyst that is solid and granular and when dried is storage stable provided that oxygen and active hydrogen compounds are excluded. Alternatively, the procatalyst is used as obtained from the hydrocarbon washing without the need for drying. The procatalyst thus produced is employed in the production of an olefin polymerization catalyst by contacting the procatalyst with a cocatalyst and a selectivity control agent.

The mixed metal-containing procatalyst serves as one component of a Ziegler-Natta catalyst system where it is contacted with a cocatalyst and optionally, a selectivity control agent. The cocatalyst component employed in the Ziegler-Natta catalyst system may be chosen from any of the known activators of olefin polymerization catalyst systems employing a transition metal halide, but organoaluminum compounds are preferred. Illustrative organoaluminum cocatalysts include trialkylaluminum compounds, alkylaluminum alkoxide compounds alkylaluminoxane compounds and alkylaluminum halide compounds in which each alkyl independently has from 2 to 6 carbon atoms inclusive. The preferred organoaluminum cocatalysts are halide free and particularly preferred are the trialkylaluminum compounds such Suitable organoaluminum cocatalysts include compounds having the formula $Al(R''')_dX_eH_f$ wherein: X is F, Cl, Br, I or OR'''', R''' and R'''' are saturated hydrocarbon radicals containing from 1 to 14 carbon atoms, which radicals may be the same or different, and, if desired, substituted with any substituent which is inert under the reaction conditions employed during polymerization, d is 1 to 3, e is 0 to 2, f is 0 or 1, and d+e+f=3. Such cocatalysts can be employed individually or in combination thereof and include compounds such as $Al(C_2H_5)_3$, $Al(C_2H_5)_2Cl$, $Al_2(C_2H_5)_3Cl_3$, $Al(C_2H_5)_2H$, $Al(C_2H_5)_2(OC_2H_5)$, $Al(i-C_4H_9)_3$, $Al(i-C_4H_9)_2H$, $Al(C_6H_{13})_3$ and $Al(C_8H_{17})_3$.

Preferred organoaluminum cocatalysts are triethyl aluminum, triisopropyl aluminum, triisobutyl aluminum and diethylhexyl aluminum. Triethyl aluminum is a preferred trialkylaluminum cocatalyst.

The organoaluminum cocatalyst also can be an aluminoxane such as methylaluminoxane (MAO) or modified methylaluminoxane (MMAO), or a boron alkyl. The method of preparing aluminoxanes is well known in the art. Aluminoxanes may be in the form of oligomeric linear alkyl aluminoxanes represented by the formula:

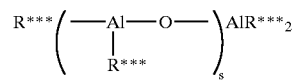

or oligomeric cyclic alkyl aluminoxanes of the formula:

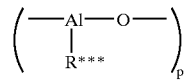

wherein s is 1–40, preferably 10–20; p is 3–40, preferably 3–20; and R* is an alkyl group containing 1 to 12 carbon atoms, preferably methyl or an aryl radical such as a substituted or unsubstituted phenyl or naphthyl radical. In the case of MAO, R* is methyl, whereas in MMAO, R* is a mixture of methyl and C2 to C12 alkyl groups wherein methyl comprises about 20 to 80 percent by weight of the R* group.

The organoaluminum cocatalyst, during formation of the olefin polymerization catalyst, is preferably employed in a molar ratio of aluminum to the mixture of T1 and T2 of the procatalyst of from about 1:1 to about 150:1, but more preferably in a molar ratio of from about 10:1 to about 100:1.

The final component of the Ziegler-Natta catalyst system is the optional selectivity control agent (SCA), or external electron donor, which typically is used when polymerizing propylene, or mixtures thereof. Typical SCAs are those conventionally employed in conjunction with titanium-based procatalysts and organoaluminum cocatalysts. Illustrative of suitable selectivity control agents are those classes of electron donors employed in procatalyst production as described above as well as organosilane compounds including alkylakoxysilanes and arylalkoxysilanes. Particularly suitable silicon compounds of the invention contain at least one silicon-oxygen-carbon linkage. Suitable silicon compounds include those having the formula $R^1_mSiY_nX_p$ wherein: $R^1$ is a hydrocarbon radical containing from 4 to 20 carbon atoms, Y is —OR$^2$ or —OCOR$^2$ wherein R$^2$ is a hydrocarbon radical containing from 1 to 20 carbon atoms, X is hydrogen or halogen, m is an integer having a value of from 0 to 3, n is an integer having a value of from 1 to 4, p is an integer having a value of from 0 to 1, and preferably 0, and m+n+p=4. R$^1$ should be such that there is at least one non-primary carbon in the alkyl and preferably, that such non-primary carbon is attached directly to the silicon atom. Examples of R$^1$ include cyclopentyl, t-butyl, isopropyl or cyclohexyl. Examples of R$^2$ include ethyl, butyl, isopropyl, phenyl, benzyl and t-butyl. Examples of X are Cl and H.

Each R$^1$ and R$^2$ may be the same or different, and, if desired, substituted with any substituent which is inert under the reaction conditions employed during polymerization. Preferably, R$^2$ contains from 1 to 10 carbon atoms when it is aliphatic and may be sterically hindered or cycloaliphatic, and from 6 to 10 carbon atoms when it is aromatic. Silicon compounds in which two or more silicon atoms are linked to each other by an oxygen atom, i.e., siloxanes or polysiloxanes, may also be employed, provided the requisite silicon-oxygen-carbon linkage is also present. The preferred selectivity control agents are alkylalkoxysilanes such as ethyltriethoxysilane, diisobutyl dimethoxysilane, cyclohexylmethyldimethoxysilane, propyl trimethoxysilane, dicyclohexyl dimethoxysilane, and dicyclopentyl dimethoxysilane. In one modification, the selectivity control agent is a portion of the electron donor added during procatalyst production. In an alternate modification the selectivity control agent is provided at the time of the contacting of procatalyst and cocatalyst. In either modification, the selectivity control agent is provided in a quantity of from 0.1 mole to about 100 moles per mole of mixture of T1 and T2 in the procatalyst. Preferred quantities of selectivity control agent are from about 0.5 mole to about 25 mole per mole of mixture of T1 and T2 in the procatalyst.

The olefin polymerization catalyst may be used in slurry, liquid phase, gas phase and liquid monomer-type reaction systems as are known in the art for polymerizing olefins. Polymerization preferably is conducted in a fluidized bed polymerization reactor, however, by continuously contacting an alpha-olefin having 2 to 8 carbon atoms with the components of the catalyst system, i.e, the solid procatalyst component, cocatalyst and optional SCAs. In accordance with the process, discrete portions of the catalyst components can be continually fed to the reactor in catalytically effective amounts together with the alpha-olefin while the polymer product is continually removed during the continuous process. Fluidized bed reactors suitable for continuously polymerizing alpha-olefins have been previously described and are well known in the art. Fluidized bed reactors useful for this purpose are described, e.g., in U.S. Pat. Nos. 4,302,565, 4,302,566 and 4,303,771, the disclosures of which are incorporated herein by reference. Those skilled in the art are capable of carrying out a fluidized bed polymerization reaction using the guidelines provided herein.

It is preferred sometimes that such fluidized beds are operated using a recycle stream of unreacted monomer from the fluidized bed reactor. In this context, it is preferred to condense at least a portion of the recycle stream. Alternatively, condensation may be induced with a liquid solvent. This is known in the art as operating in "condensing mode." Operating a fluidized bed reactor in condensing mode generally is known in the art and described in, for example, U.S. Pat. Nos. 4,543,399 and 4,588,790, the disclosures of which are incorporated by reference herein in their entirety. The use of condensing mode has been found to lower the amount of xylene solubles in isotactic polypropylene and improve catalyst performance when using the catalyst of the present invention.

The catalyst composition may be used for the polymerization of olefins by any suspension, solution, slurry, or gas phase process, using known equipment and reaction conditions, and is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000, preferably 50 to 400 psi, most preferably 100 to 300 psi, and temperatures in the range of 30 to 130° C., preferably 65 to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,528,790 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum.

The precise procedures and conditions of the polymerization are broadly conventional but the olefin polymerization process, by virtue of the use therein of the polymerization catalyst formed from the solid precursor, provides polyolefin product having a relatively high bulk density in quantities that reflect the relatively high productivity of the olefin polymerization catalyst. In addition, the polymeric products produced in the present invention have a reduced level of fines.

Conventional additives may be included in the process, provided they do not interfere with the operation of the catalyst composition in forming the desired polyolefin.

When hydrogen is used as a chain transfer agent in the process, it is used in amounts varying between about 0.001 to about 10 moles of hydrogen per mole of total monomer feed. Also, as desired for temperature control of the system, any gas inert to the catalyst composition and reactants can also be present in the gas stream.

The polymerization product of the present invention can be any product, homopolymer, copolymer, terpolymer, and the like. Usually, the polymerization product is a homopolymer such as polyethylene or polypropylene, particularly polypropylene. Alternatively, the catalyst and process of the invention are useful in the production of copolymers including copolymers of ethylene and propylene such as EPR and polypropylene impact copolymers when two or more olefin monomers are supplied to the polymerization process. Those skilled in the art are capable of carrying out suitable polymerization of homopolymers, copolymers, terpolymers, etc., using liquid, slurry or gas phase reaction conditions, using the guidelines provided herein.

Ethylene polymers of the invention include ethylene homopolymers, and interpolymers of ethylene and linear or branched higher alpha-olefins containing 3 to about 20 carbon atoms, with densities ranging from about 0.90 to about 0.95 and melt indices of about 0.005 to 1000. Suitable higher alpha-olefins include, for example, propylene, 1-butene, 1-pentene, 1-hexene, 4-methyl-1-pentene, 1-octene, and 3,5,5-trimethyl 1-hexene. Cyclic olefins such as vinyl cyclohexane or norbornene may also be polymerized with the ethylene. Aromatic compounds having vinyl unsaturation, such as styrene and substituted styrenes, may also be included as comonomers. Particularly preferred ethylene polymers comprise ethylene and about 1 to about 40 percent by weight of one or more comonomers described above.

The invention will now be illustrated by examples exemplifying particularly preferred embodiments thereof. Those skilled in the art will appreciate that these examples do not limit the invention but rather serve to more fully describe particularly preferred embodiments.

EXAMPLES

In the examples, the following terms are defined as follows:

Glossary:

MI is the melt index (optionally termed $I_2$), reported as grams per 10 minutes, determined in accordance with ASTM D-1238, condition E, at 190° C.

FI is the flow index (optionally termed $I_{21}$), reported as grams per 10 minutes, determined in accordance with ASTM D-1238 condition F, and was measured at ten times the weight used in the melt index test.

MFR is the melt flow ratio, which is the ratio of flow index to melt index. It is related to the molecular weight distribution of the polymer.

For high molecular weight polymers an optional melt index is taken using the same conditions except using a 5.0 Kg weight. The melt index under that condition is termed $I_5$ and the melt flow ratio $I_{21}/I_5$ is termed $MFR_5$. As above, larger values of $MFR_5$ imply broader molecular weight distribution Productivity is given in Kg polymer/g procatalyst/hour/100 psi ethylene.

Example 1

Magnesium, Iron, Titanium-containing Complex

Preparation of Precursor

A polymerization procatalyst precursor comprising a mixture of magnesium, titanium and iron was prepared in accordance with the following reaction:

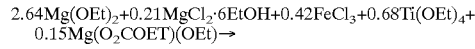

Approximately 0.6 g magnesium ethyl carbonate (CMEO, carbonized magnesium ethoxide: 3.8 mmol), 7.55 g of $Mg(OEt)_2$ (66 mmol), 1.74 g of Fe $Cl_3$ (10.5 mmol), and 1.95 g $MgCl_2 6EtOH$ (5.2 mmol) were mixed in an 8 ounce bottle. To this mixture, 100 gm of chlorobenzene (90 ml) then was added. The mixture was stirred for about one minute, and then 4.11 g of $Ti(OEt)_4$ (95%, 17.1 mmol) was added. The resulting mixture (still in the 8 ounce bottle) was placed in a 100° oil bath and stirred at 440 rpm. After 27 minutes (96° oil), only a few of the granules had dissolved, but there was some precipitate evident in the brown liquid. By 3 hr, 47 min (97° oil), there were still granules present in a very thick slurry. By 5 hr, 41 min, the slurry was so thick that the stir speed was increased to 550 rpm, and a gentle nitrogen flow was started. At 6 hr, 39 min, the stir speed was increased to 660 rpm and 40 ml of heptane was added over a period of 15 minutes. The heat was then turned of and the slurry allowed to stir overnight. The mixture was filtered in the glovebox. The solids were washed once with chlorobenzene, then twice with hexane and sucked dry to yield 11.8 g of beige powder.

Preparation of Polymerization Procatalyst

Approximately 2.12 g of the precursor prepared above was slurried in 15 ml of hexane. About 11 ml of 25% EADC/toluene then was added to the slurry over a period of about 3 minutes. The initially tan slurry turned to greyish brown. After stirring for 20 minutes, the slurry was filtered. The solids were washed twice with hexane and dried under moving nitrogen to yield 2.15 g of grey powder. That powder was slurried in 15 ml of hexane then 11 ml of 25% EADC/toluene was added over 2 minutes. The initially grey slurry turned brown. After 20 minutes of stirring, the mixture was filtered. The solids were washed four times with hexane and then dried under moving nitrogen to produce 1.57 g of tan powder. Analysis of the solid tan powder revealed: 3.50% Ti, 3.09% Fe, 12.7% Mg, 4.64% Al. A polymerization sample was made by slurrying 0.100 g of catalyst in 20 ml of Kaydol oil (0.60% solids).

Slurry Polymerizations

A. To a one liter stainless steel (SS) reactor, containing 500 ml of hexane and 15 ml of 1-hexene, were added 341 standard cubic centimeters (SCC) of $H_2$ (13 psi partial pressure). Triethyl aluminum (0.25 mmol of 1.56 M heptane solution) was injected by syringe. The catalyst (0.4 ml of 0.60% slurry of procatalyst prepared above) was injected from a 50 ml bomb using ethylene pressure and about 20 ml of hexane. After polymerizing for 30 minutes at 85° C., while adding ethylene on demand to keep the total pressure at 160 psi, the reaction was extinguished by injecting 2 ml of isopropanol. The catalyst decay rate had been 67%/20 minutes. The collected polymer was allowed to air dry overnight before characterization. The polymerization produced 181 g of polymer of 0.25 g/cc bulk density with melt index ($I_2$) of 0.204 dg/min and flow index ($I_{21}$) of 6.88 dg/min (MFR=34). The polymer density was determined to be 0.9459 g/cc. Size exclusion chromatography showed Mw/Mn=7.8.

B. Polymerization with diene comonomer: The polymerization of part A above was repeated except that the amount of catalyst slurry was increased to 0.7 ml and 5.0 ml of 5-vinyl-2-norbornene was added to the reactor. This polymerization produced about 181 g of polymer of 0.22 g/cc bulk density with I5 of 0.165 dg/min and flow index ($I_{21}$) of 6.88 dg/min ($I_{21}/I_5$=24, corrresponding to an MFR>100). Size exclusion chromatography showed Mw/Mn=10.9.

Example 2
Magnesium and Tin-containing complex
Preparation of Precursor

A polymerization procatalyst precursor comprising a mixture of magnesium and tin was prepared in accordance with the following reaction:

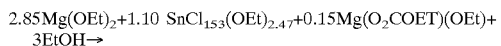

NaOEt (4.72 g, 96%, 67.9 mmol) was slurried into 50 ml of chlorobenzene in a 4 ounce bottle then SnCl$_4$ (7.16 g, 3.22 ml, 27.5 mmol) was added. Ethanol (3.46 g, 75 mmol) was then added while stirring at room temperature. After about 10 minutes at room temperature, the mixture was transferred to a 75° C. oil bath and stirring continued for one hour. Heating was terminated and the mixture allowed to cool overnight. The solution (containing the tin ethoxychloride) was decanted from the sludge of sodium salts and into an 8 ounce bottle. To this solution was added a mixture of Mg(OEt)$_2$ (8.15 g, 71.2 mmol) and carbonized magnesium ethoxide (0.6 g, 3.8 mmol) which had been slurried in 45 ml of chlorobenzene. The bottle was placed in a 100° C. oil bath and stirred for 5.5 hours at 440 rpm by which time nearly all of the magnesium ethoxide granules appeared to have reacted. The bottle cap was removed and a gentle stream of nitrogen was passed over the reaction for about 90 minutes whereupon about 7% of the solvent had evaporated. The mixture was transferred to a glovebox and filtered warm. The solids were washed once with chlorobenzene and twice with hexane then dried under moving nitrogen. Obtained were 6.15 g of cream colored powder composed largely of glassy particles about 5 microns in diameter.

Example 3
Magnesium, Vanadium (+4), Titanium-containing Complex
Preparation of Precursor A polymerization procatalyst precursor comprising a mixture of magnesium, titanium and vanadium (+4) was prepared in accordance with the following reaction:

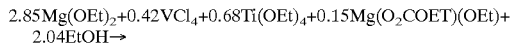

Carbonized magnesium ethoxide (0.6 g, 3.8 mmol), 8.15 g Mg(OEt)$_2$ (8.15 g, 71.2 mmol) and Ti(OEt)$_4$ (4.11 g, 95%, 17.1 mmol) were added to 100 g of chlorobenzene in an 8 ounce bottle. The mixture was stirred a minute then VCl$_4$ (2.00 g, 10.4 mmol) was added. The bottle, containing the dark green slurry, was placed in a 100° C. oil bath then 3.0 ml of Ethanol (2.36 g, 51.1 mmol) was quickly added. Stirring was continued overnight at 440 rpm by which time all of the magnesium ethoxide granules appeared to have reacted. A gentle nitrogen flow was passed over the surface of the reaction and was continued for 70 minutes until about 4% of the solvent had evaporated. Heating was stopped and the slurry was allowed to stir and cool to room temperature then filtered. The solids were washed twice with chlorobenzene and twice with hexane then dried under moving nitrogen. Obtained were 11.0 g of pale green powder composed of predominately two sizes of translucent granules clustered about 10 micron and 20 micron diameter.

Example 4
Magnesium, Vanadium (+5), Titanium-containing Complex
Preparation of Precursor A polymerization procatalyst precursor comprising a mixture of magnesium, vanadium (+4) and vanadium (+5) was prepared in accordance with the following reaction:

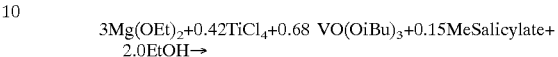

Mg(OEt)$_2$ (8.58 g, 75 mmol), VO(OiBu)$_3$ (4.9 g, 17.1 mmol) and 0.57 g of methyl salicylate (3.75 mmol) were mixed with 100 gm of chlorobenzene (90 ml), in an 8 ounce bottle. After stirring a minute, TiCl$_4$ (1.97 g, 10.4 mmol) was added. The bottle was placed in a 100° C. oil bath, then Ethanol (2.36 g, 51 mmol) was quickly added to give a green slurry. By 60 minutes stirring at 440 rpm the slurry had turned yellow and there were still many granules of unreacted magnesium ethoxide. By 4.5 hours nearly all of the granules appeared to have reacted. A gentle nitrogen stream was passed over the reaction surface as 6% of the solvent evaporated in 1.5 hours. The heat was removed and the slurry allowed to stir and cool to room temperature then filtered. The solids were washed once with chlorobenzene and once with hexane then dried under moving nitrogen. Obtained were 7.6 g of pastel yellow powder.

Example 5
Magnesium, Vanadium (+5), Vanadium (+4)-containing Complex
Preparation of Precursor A polymerization procatalyst precursor comprising a mixture of magnesium, vanadium (+5) and vanadium (+4) was prepared in accordance with the following reaction:

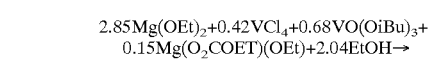

Mg(OEt)$_2$ (8.15 g, 71.2 mmol), VO(OiBu)$_3$ (4.9 g, 17.1 mmol) and 0.6 g of carbonized magnesium ethoxide (0.6 g, 3.8 mmol) were mixed with 100 gm of chlorobenzene (90 ml), in an 8 ounce bottle. After stirring a minute, VCl$_4$ (2.0 g, 10.4 mmol) was added. The bottle was placed in a 96° C. oil bath then ethanol (2.36 g, 51 mmol) was quickly added to give a slurry of granules in a dark green solution. By seven hours, stirring at 440 rpm, a clumpy slurry had been obtained. The cap was removed and the and stirring continued under a gentle flow of nitrogen to evaporate the excess ethanol (about 5% of the solvent). After cooling to room temperature, the supernatant was decanted from the clumpy precipitate. The clumps were then resuspended in fresh chlorobenzene and stirred overnight to produce a homogeneous slurry. The slurry was filtered, then the solids washed twice with chlorobenzene and twice with hexane and dried under moving nitrogen. Obtained were 9.90 g of pastel green powder.

Example 6
Magnesium Iron, Titanium-containing Complex
Preparation of Precursor A polymerization procatalyst precursor comprising a mixture of magnesium, titanium and iron was prepared in accordance with the following reaction:

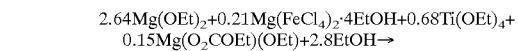

Mg(OEt)$_2$ (7.55 g, 66 mmol), carbonized magnesium ethoxide (0.6 g, 3.8 mmol), and Mg(FeCl$_4$)$_2$·4EtOH (3.1 g, 5.2 mmol) were slurried into 130 g of chlorobenzene in an 8 ounce bottle. After stirring about a minute, Ti(OEt)$_4$ (95%, 4.11 g, 17.1 mmol) was added. The bottle was placed in a 100° C. oil bath, and then ethanol (3.22 g, 70 mmol) was quickly added to obtain a pale green slurry. After stirring at 440 rpm for 3.7 hours, a gentle nitrogen flow was passed over the reaction surface until about 6% of the solvent had evaporated. The precipitate had formed one large clump. After standing overnight at room temperature, the clump had become brittle and was easily broken to form a homogeneous slurry which was stirred another day in a 77° C. oil bath then filtered. The solids were washed once with chlorobenzene and twice with hexane then dried under moving nitrogen to obtain 8.0 g of white powder.

Example 7
Manganese and Titanium-containing complex
Preparation of Precursor A polymerization procatalyst precursor comprising a mixture of manganese and titanium was prepared in accordance with the following reaction:

3Mn(OEt)$_2$+0.42TiCl$_4$+0.68Ti(OEt)$_4$+0.1HOC$_6$H$_4$CO$_2$Me+ 3.4EtOH→ 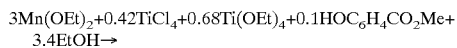

Mn(OEt)$_2$ (5.44 g, 37.5 mmol) was mixed with 50 gm of chlorobenzene, in a 4 ounce bottle then Ti(OEt)$_4$ (2.06 g, 95%, 8.55 mmol) was added. After stirring for about one minute, methyl salicylate (0.19 g, 1.25 mmol) was added and stirring continued as TiCl$_4$ (0.985 g, 5.7 mmol) was added. The bottle was placed in a 95° C. oil bath, and then Ethanol (1.96 g, 42.5 mmol) was added quickly and stirring continued at 440 rpm for 3.4 hours. The bottle cap was then removed and a nitrogen stream was passed over the reaction surface for 15 minutes whereupon 10% of the solvent evaporated. The mixture was transferred to a glovebox and filtered warm. The solids were washed twice with chlorobenzene and twice with hexane then dried under moving nitrogen. Obtained were 4.63 g of brown powder.

Example 8
Magnesium, Manganese, Zirconium-containing Complex
Preparation of Precursor A polymerization procatalyst precursor comprising a mixture of manganese and zirconium was prepared in accordance with the following reaction:

2.1Mg(OEt)$_2$+0.90MnCl$_2$+0.45Zr(OEt)$_4$+0.60Zr(OBu)$_4$+ 0.15HOC$_6$H$_4$CO$_2$Me+3.7EtOH→ 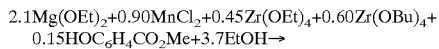

MnCl$_2$ (2.83 g, commercially available from Aldrich, 98% flakes, ~22.5 mmol) was stirred with 5.4 ml Ethanol, in an 8 ounce bottle, for 25 minutes in a 100° C. oil bath to produce a thin, grey mud. After cooling for 10 minutes, 100 g of chlorobenzene was added followed by Mg(OEt)$_2$ (6.01 g, 52.5 mmol), Zr(OEt)$_4$ (3.05 g, 11.25 mmol) and Zr(OBu)$_4$ (6.60 g, 87.5%, 15 mmol). After stirring about one minute, methyl salicylate (0.57 g, 3.75 mmol) was added. The bottle was placed in a 100° C. oil bath and stirred for 2 hours at 440 rpm to obtain a cloudy brown, nearly translucent, slurry. The cap was removed and a gentle nitrogen flow maintained above the reaction surface for an hour while about 6% of the solvent had evaporated. The resulting slurry was transferred to a glovebox and filtered warm. The solids were washed once with chlorobenzene and twice with hexane then dried under moving nitrogen to obtain 8.74 g of pale gray powder consisting predominately of granular particles of about 15 micron diameter.

Example 9
Magnesium, Tin Titanium-containing Complex
Preparation of Precursor A polymerization procatalyst precursor comprising a mixture of magnesium, titanium and tin was prepared in accordance with the following reaction:

2.85Mg(OEt)$_2$+0.42SnCl$_4$+0.68Ti(OEt)$_4$ +0.15Mg(O$_2$COET)(OEt)+3EtOH→ 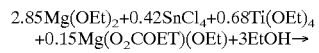

Mg(OEt)$_2$ (8.15 g, 71.2 mmol) and carbonized magnesium ethoxide (0.6 g, 3.8 mmol) were mixed with 100 gm of chlorobenzene in an 8 ounce bottle, and then Ti(OEt)$_4$ (4.11 g, 95%, 17.1 mmol) was added. After stirring about one minute, SnCl$_4$ (2.71 g, 10.4 mmol) was added. The bottle was placed in a 100° C. oil bath, and then Ethanol (3.46 g, 75 mmol) was quickly added. The mixture was stirred for 3.75 hours at 440 rpm to obtain a cloudy, translucent slurry with only a few granules of magnesium ethoxide appearing to remain unreacted. The cap was removed and a gentle nitrogen stream was pased over the reaction for 90 minutes as about 7% of the solvent evaporated. The mixture was transferred to a glovebox and filtered warm. The solids were washed once with chlorobenzene and twice with hexane then dried under moving nitrogen. Obtained were 11.8 g of white powder composed of translucent granules all of which were about 15 microns in diameter. Elemental analysis revealed 12.0% Mg, 3.59% Ti and 9.67% Sn.

Example 10
Magnesium, Hafnium and Titanium-containing Complex
Preparation of Precursor A polymerization procatalyst precursor comprising a mixture of magnesium, hafnium and titanium was prepared in accordance with the following reaction:

3Mg(OEt)$_2$+0.40HfCl$_4$+0.65Ti(OEt)$_4$+0.15HOC$_6$H$_4$CO$_2$Me+ 3.7EtOH→ 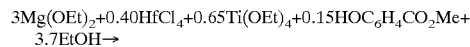

Ti(OEt)$_4$ (3.96 g, 95%, 16.25 mmol) and HfCl$_4$ (3.20 g, 10 mmol) were mixed with Ethanol (4.24 g, 92 mmol) in an 8 ounce bottle then methyl salicylate (0.57 g, 3.75 mmol) was added. The mixture was stirred for 30 minutes at about 60° C. to obtain a yellow-orange solution then 100 g of chlorobenzene was added. After thorough mixing, Mg(OEt)$_2$ (8.58 g, 75 mmol) was added. The bottle was then placed in a 97° oil bath and stirred 3.3 hours at 440 rpm when 0.96 g of butanol was added. After another 105 minutes all of the magnesium ethoxide granules appeared to have reacted. The cap was then removed and a gentle flow of nitrogen was passed over the reaction for 67 minutes as 5% of the solvent evaporated. Heating was then halted and the slurry allowed to stir and cool overnight. The slurry was transferred to a glovebox and filtered. The solids were washed once with chlorobenzene and twice with hexane then dried under moving nitrogen. Obtained were 9.66 g of white powder consisting predominately of translucent particles of 5 to 10 microns in diameter.

Example 10b
Magnesium and Hafnium-containing Complex
Preparation of Precursor A polymerization procatalyst precursor comprising a mixture of magnesium and hafnium was prepared in accordance with the following reaction:

3Mg(OEt)$_2$+0.40HfCl$_4$+0.65Hf(OEt)$_4$+0.15HOC$_6$H$_4$CO$_2$Me+ 3.7EtOH→ 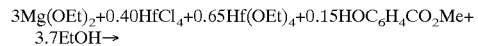

Hf(OEt)$_4$ (5.82 g, 16.25 mmol) and of HfCl$_4$ (3.20 g, 10 mmol) were mixed as powders in an 8 ounce bottle. Ethanol (4.24 g, 92 mmol) and methyl salicylate (0.57 g, 3.75 mmol) were then added and the mixture stirred for 45 minutes at 60° C. to obtain, a clear, viscous solution. To this solution was added 50 g of chlorobenzene followed by Mg(OEt)$_2$ (8.58 g, 75 mmol) and another 50 g of chlorobenzene. The bottle was placed in a 100° C. oil bath and stirred for 2.7 hours at 440 rpm whereupon all of the magnesium ethoxide granules appeared to have reacted to produce a translucent slurry. The bottle cap was removed and a gentle stream of nitrogen passed over the reaction for 67 minutes as 10% of the solvent evaporated. After cooling overnight, the mixture was transferred to a glovebox and filtered. The solids were washed once with chlorobenzene and twice with hexane then dried under moving nitrogen. Obtained were 11.5 g of white powder composed of granules ranging between 10 to 30 microns in diameter.

Example 11
Magnesium, Titanium (+3), Titanium (+4)-containing Complex
Preparation of Precursor A polymerization procatalyst precursor comprising a mixture of magnesium, titanium (+3) and titanium (+4) was prepared in accordance with the following reaction:

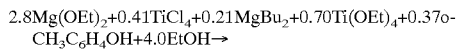
2.8Mg(OEt)$_2$+0.41TiCl$_4$+0.21MgBu$_2$+0.70Ti(OEt)$_4$+0.37o-CH$_3$C$_6$H$_4$OH+4.0EtOH→

TiCl$_4$ (1.94 g, 10.25 mmol) was dissolved in 100 g of chlorobenzene in an 8 ounce bottle. While stirring vigorously a solution of 14% Bu$_2$ Mg in heptane (5.06 g, 5.1 mmol) was added. After stirring two days at room temperature, Mg(OEt)$_2$ (8.0 g, 69.9 mmol), o-cresol (1.00 g, 9.25 mmol) and Ti(OEt)$_4$ (4.20 g, 95%, 17.5 mmol) were added. The bottle was placed in a 100° C. oil bath, and then Ethanol (3.94 g, 85.5 mmol) was added quickly and stirring continued for 2.4 hours at 440 rpm whereupon all of the magnesium ethoxide granules appeared to have reacted. The bottle cap was removed and a gentle flow of nitrogen was passed over the reaction for about one hour as about 8% of the solvent evaporated. The mixture was transferred to a glovebox and filtered warm (a green filtrate was obtained). The solids were washed once with chlorobenzene and twice with hexane then dried under moving nitrogen. Obtained were 12.0 g of light green fluffy powder composed of granules clustered around 10 to 15 microns in diameter.

Example 11b
Magnesium, Titanium (+3), Titanium (+4)-containing Complex
Preparation of Precursor A polymerization procatalyst precursor comprising a mixture of magnesium, titanium (+3) and titanium (+4) was prepared in accordance with the following reaction:

3Mg(OEt)$_2$+0.28TiCl$_3$+0.2TiCl$_4$+0.63Ti(OEt)$_4$+0.37o-CH$_3$C$_6$H$_4$OH+3.46 EtOH→

Mg(OEt)$_2$ (8.6 g, 75 mmol) and TiCl$_3$ (1.08 g, 7.0 mmol) were mixed with 100 g of chlorobenzene in an 8 ounce bottle. Ortho-cresol (o-cresol, 1.00 g, 9.25 mmol), TiCl$_4$ (0.95 g, 5.0 mmol) and Ti(OEt)$_4$ (3.36 g, 95%, 14.0 mmol) were then added. The bottle was then placed in a 102° C. oil bath, and then Ethanol (3.96 g, 85.9 mmol) was added quickly. The black slurry was stirred for 42 minutes at 440 rpm whereupon all of the magnesium ethoxide granules appeared to have reacted to obtain a dark green slurry. The bottle cap was removed and a gentle nitrogen flow was passed over the reaction for 42 minutes while 7% of the solution evaporated. The slurry was transferred to a glovebox and filtered warm. The solids were washed once with chlorobenzene and twice with hexane, and then dried under moving nitrogen. Obtained were 12.1 g of pale green powder composed predominately of lemon-drop shaped particles of about 10 to 12 microns in diameter.

Example 12
Magnesium, Tin, Titanium(+3/+4)-containing Complex
Preparation of Precursor A polymerization procatalyst precursor comprising a mixture of magnesium, titanium(+3/+4) and tin was prepared in accordance with the following reactions:

0.68Ti(OEt)$_4$+0.21MgBu→     A

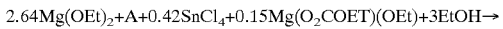
2.64Mg(OEt)$_2$+A+0.42SnCl$_4$+0.15Mg(O$_2$COET)(OEt)+3EtOH→

Ti(OEt)$_4$ (4.11 g, 95%, 17.1 mmol Ti, 4.46 mmol Ethanol) was dissolved in 100 g of chlorobenzene in an 8 ounce bottle under nitrogen atmosphere. With stirring, a 1.0 M solution of Bu$_2$ Mg in heptane (7.33 ml, 5.23 g; 7.33 mmol, extra was added to react with the 5% Ethanol from the Ti(OEt)$_4$) was added and the royal blue colored slurry was allowed to stir overnight at room temperature. To that stirring slurry was added SnCl$_4$ (2.71 g, 10.4 mmol) followed by Mg(OEt)$_2$ (7.31 g, 63.9 mmol) and carbonized magnesium ethoxide (0.6 g, 3.8 mmol. The bottle was capped and placed in a 100° C. oil bath then Ethanol (3.46 g, 75 mmol) was added quickly to give a gray slurry. The mixture was allowed to stir at 440 rpm for 2 hours whereupon all of the magnesium ethoxide granules appeared to have reacted to produce a cloudy slurry. The cap was removed and a gentle nitrogen stream was pased over the reaction until about 7% of the solvent had evaporated. The reaction was transferred to a glovebox and filtered warm. The solids were washed once with chlorobenzene and twice with hexane then dried under moving nitrogen. Obtained were 11.0 g of gray powder composed translucent granules in the range of 15–20 microns in diameter.

Example 13
Magnesium, Titanium (+3), Titanium (+4)-containing Complex
Preparation of Precursor A polymerization procatalyst precursor comprising a mixture of magnesium, titanium (+3) and titanium (+4) was prepared in accordance with the following reaction:

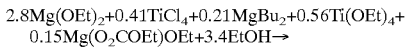
2.8Mg(OEt)$_2$+0.41TiCl$_4$+0.21MgBu$_2$+0.56Ti(OEt)$_4$+0.15Mg(O$_2$COEt)OEt+3.4EtOH→

TiCl$_4$ (1.94 g, 10.25 mmol) was dissolved in 90 g of nitrogen degassed chlorobenzene in an 8 ounce bottle. While stirring vigorously, a solution of 1.0 M Bu$_2$ Mg in heptane (5.1 ml, 3.64 g, 5.1 mmol) was added. After stirring an hour at about 50° C., Mg(OEt)$_2$ (8.0 g, 69.9 mmol) and Ti(OEt)$_4$ (3.36 g, 95%, 14 mmol) were added followed by a mixture of {0.6 g carbonized magnesium ethoxide (3.8 mmol) +3.14 g ethanol (68 mmol) +1.21 g butanol (16 mmol)}. The bottle was placed in a 100° C. oil bath and the walls rinsed with 10 g of chlorobenzene and the deep brown slurry stirred for 3.1 hours at 440 rpm whereupon nearly all of the magnesium ethoxide granules appeared to have reacted. The bottle cap was removed and a gentle flow of nitrogen was passed over the reaction for about one hour as about 15% of the solvent evaporated. Heating was halted and the mixture was allowed to stir and cool for 3 days then transferred to a glovebox and filtered. The solids were washed once with chlorobenzene and twice with hexane then dried under moving nitrogen. Obtained were 12.8 g of green powder composed of granules clustered around 5 microns in diameter.

Example 14
Magnesium and Iron-containing Complex
Preparation of Precursor

A polymerization procatalyst precursor comprising a mixture of magnesium and iron was prepared in accordance with the following reaction:

$$2.8Mg(OEt)_2 + 1.05FeCl_3 + 0.2MgBr_2 \cdot 4EtOH \rightarrow$$ 

$MgBr_2 \cdot 4EtOH$ (1.84 g, 5.0 mmol), $Mg(OEt)_2$ (8.01 g, 70 mmol) and $FeCl_3$ (4.26 g, 26.3 mmol) were slurried into 100 gm of chlorobenzene in an 8 ounce bottle. The bottle was placed in a 100° C. oil bath and stirred for 3.7 hours at 440 rpm. All of the magnesium ethoxide granules appeared to have reacted and a uniform slurry was obtained. The bottle cap was removed and a gentle nitrogen flow was maintained above the reaction surface for an hour as about 6% of the solvent evaporated. The slurry was transferred to a glovebox and filtered warm. The solids were washed once with chlorobenzene and twice with hexane then dried under moving nitrogen. Obtained were 12.6 g of tan powder consisting of particles of 5–10 microns in diameter.
Preparation of Polymerization Procatalysts Polymerization procatalysts were prepared from approximately 2.1–2.3 g of each of the precursors of Examples 2-, 11 by contacting with ethylaluminum dichloride according to the procedure outlined in Example 1 above.

A polymerization procatalyst was prepared from approximately 2.3 g of the precursor of Example 12 by contacting with ethylaluminum dichloride according to the procedure outlined in Example 1 above except that only a single wash of 12 ml of 25% ethylaluminum in toluene was used.

A polymerization procatalyst was prepared from approximately 2.5 g of the precursor of Example 13 by contacting with ethylaluminum dichloride according to the procedure outlined in Example 1 above except that only a single wash of 16 ml of 25% ethylaluminum in toluene was used.

Approximately 2.25 g of the precursor of Example 14 was slurried in 20 ml of hexane. About 11 ml of a toluene solution containing 20% $SiCl_4$ and 5% $TiCl_4$ then was added to the slurry over a period of about 3 minutes. The initially tan slurry turned to orange-red. After shaking for 60 minutes, the slurry was filtered. The solids were washed twice with hexane and dried under moving nitrogen to yield 2.46 g of an orange-yellow solid powder. That powder was slurried in 20 ml of hexane, and then a mixture of 11 ml of 25% EADC/toluene and 3.5 ml of a 1.0 M $BCl_3$/hexane solution was added over 2 minutes. The initially red-orange slurry turned brown. After 60 minutes of shaking, the mixture was filtered. The solids were washed four times with hexane and then dried under moving nitrogen to produce 1.88 g of brown powder. Analysis of the solid tan powder revealed: 2.84% Ti, 7.40% Fe, 14.2% Mg, 2.64% Al. A polymerization sample was made by slurrying 0.100 g of catalyst in 20 ml of Kaydol oil (0.60% solids).
Slurry Polymerizations The procatalysts prepared above were polymerized using the procedure outlined in Example 1 (Part A) above. Except as noted in the following table, each polymerization used about 0.5 ml of the approximately 0.6% mineral oil procatalyst slurry (approximately 2.5 mg procatalyst), 0.26 ml of 1.56 M triethylaluminum/heptane solution, 280–360 standard cc of hydrogen, 15 ml of hexene in a diluent of 500 ml of hexane. Polymerizations were carried out for a period of 30 minutes and the polymerization polymer yields were linearly extrapolated to one hour to obtain productivity as Kg polymer/g catalyst/100 psi ethylene/hour. Decay is presented as the decline in ethylene consumption over the last 20 minutes of the polymerization. The flow ratio is given as either $I_{21}/I_5$ or as MFR (values in parentheses).

TABLE

Slurry Polymerization Results

| Precursor Ex. # | Producty Kg/g cat | b.d. g/cc | FI dg/min | I21/I5 (MFR) | decay %/20 min |
|---|---|---|---|---|---|
| 1 | 126 | 0.253 | 6.88 | (34) | 57% |
| 2 | 0.04 | | | | |
| 3 | 70.6 | 0.276 | 12.6 | (39) | 40% |
| 4 | 85.6 | 0.269 | 9.66 | (34) | 56% |
| 5 | 4.47* | 0.317 | >1000 | — | 66% |
| 6 | 77.8 | 0.278 | 12.2 | (35) | 45% |
| 7 | 8.0** | | 1.1 | 26 | 41% |
| 8 | 1.2*** | 0.253 | 8.67 | 21 | 42% |
| 9 | 76.3 | 0.246 | 7.78 | (32) | 56% |
| 10 | 33.8 | 0.172 | 9.05 | 11 | 42% |
| 11 | 101.1 | 0.327 | 3.28 | 11 | 51% |
| 12 | 58.1 | 0.245 | 12.5 | 10 | 40% |
| 13 | 103.7 | 0.303 | 11.3 | 11 | 38% |
| 14 | 43.6 | 0.307 | 3.67 | (31) | 46% |

*0.1 mmol ethyltrichloroacetate + 0.4 mmol DEAC added to reactor
**208 scc $H_2$
***1.0 mmol Al(iBu)$_3$, 1200 scc of $H_2$

Example 15
Magnesium, Samarium, Titanium-containing Complex
Preparation of Precursor A polymerization procatalyst precursor comprising a mixture of magnesium, samarium and iron was prepared in accordance with the following reaction:

$$3Mg(OEt)_2 + 0.56SmCl_3 + 0.68Ti(OEt)_4 + 0.15HOC_6H_4CO_2Me + 4.05ROH \rightarrow$$ 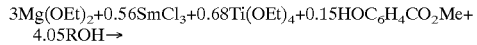

$Mg(OEt)_2$ (8.6 g, 75 mmol) and 2.11 g Of $SmCl_3$ (14.0 mmol) were mixed with 100 gm of chlorobenzene (90 ml), in an 8 ounce bottle, then 4.11 g of $Ti(OEt)_4$ (95%, 17.1 mmol) was added. After stirring a minute, methyl salicylate (0.38 g, 2.5 mmol) was added. The bottle was placed in a 105° C. oil bath, and then a mixture of 5.0 ml of ethanol (3.92 g, 85 mmol) and 1.5 ml of butanol (1.21 g, 16.3 mmol) was quickly added and the mixture stirred at 440 rpm. After an hour the slurry had begun to form clumps so the stirring rate was increased to 660 rpm. After another 45 minutes additional ethanol (6 ml) was added to disperse the clumps. After a total time of 2 hours, it was evident that some $Mg(OEt)_2$ remained unreacted, so another 1.08 g of salicyl aldehyde were added. At 4 hours total time, only a few granules remained in the blood red solution so the heat was turned off to let the solution stir and cool. After several hours cooling, during which crystals had precipitated on the walls, the oil bath was raised to 60° and about ⅓ of the solvent was evaporated under a gentle nitrogen stream. The slurry was filtered and the solids washed twice with chlorobenzene, twice with hexane the sucked dry to yield 6.0 g of translucent white chunky aggregates composed of 20–35 m particles of crystalline appearance.
Slurry Polymerization.

A procatalyst was not prepared directly from this precursor. Instead a chlorinating agent, in the form of diethylaluminum chloride, was added to the polymerization reactor along with the precursor. To a one liter stainless steel reactor, containing 500 ml of hexane and 15 ml of 1-hexene, were added 894 standard cubic centimeters (SCC) of $H_2$ (20 psi partial pressure). Triethyl aluminum (0.25 mmol of 1.56 M heptane solution) was injected by syringe. The catalyst (4.7 ml of 1.2% slurry of the Mg/Ti/Sm precursor) was injected from a 50 ml bomb using ethylene pressure and about 20 ml of hexane. Ethylene was added to a total pressure of 158 psi. After 10 minutes no ethylene had been consumed so 1.5 ml of 1.5 M diethylaluminum chloride/heptane solution was injected into the reactor by syringe whereupon polymerization began. After polymerizing for 30 minutes at 85° C., while adding ethylene on demand to keep the total pressure at 158 psi, the reaction was extinguished by injecting 2 ml of isopropanol. The catalyst decay rate had been 65%/20 minutes. The collected polymer was allowed to air dry overnight before characterization. The polymerization produced 47.7 g of polymer corresponding to a productivity of about 11.9 Kg polymer/gm catalyst/100 psi ethylene/hour.

As can be seen from the above examples, a variety of mixed metal-containing precursors can be prepared, which in turn produce highly active polymerization procatalysts. The mixed metal precursors of the invention, when converted to polymerization procatalysts, produce polymers having high bulk density and a range of molecular weight distributions, and the catalysts have modest catalyst decay. Using the guidelines provided herein, those skilled in the art are capable of tailoring polymerization procatalysts to provide a variety of catalyst decay rates and polymers having a variety of molecular weight distributions. The inventive examples also provide polymerization procatalysts that retain the excellent morphology of the precursor to thereby generate polymer having fewer fines, as well as a lower xylene solubles content.

While the invention has been described in detail with reference to particularly preferred embodiments, those skilled in the art appreciate that various modifications can be made without departing from the spirit and scope thereof all documents referred to herein are incorporated by reference herein in their entirety.

What it claimed is:

1. A process for making a solid procatalyst precursor composition comprising alkoxide groups, chloride groups, and one or more metals, M, in the +2 oxidation state selected from the group consisting of Mg, Ca, Mn, Cu, Co and Zn, and one or more metals, T, in the +3, +4 or +5 oxidation state selected from the group consisting of Ti, Zr, V, Sm, Fe, Sn, Ni, Rh, Co, Cr, Mo, W and Hf, wherein the molar ratio of M/T in the composition is from 2.5 to 3.75, with the proviso that if M is Mg alone, then T cannot consist solely of Zr, Ti, or a mixture thereof; said process comprising contacting in an inert reaction diluent one or more alkoxide containing compounds of one or more metals M, one or more alkoxide containing compounds of one or more metals, T, and a halide compound selected from the group consisting of $TiCl_3$, $TiCl_4$, $VCl_4$, $FeCl_3$, $SnCl_4$, $HfCl_4$, $MnCl_2$, $MgCl_2$ and $SmCl_3$, the molar ratio, M/T of the contacted compounds, being from 2.5 to 3.5, and removing the diluent to recover the resulting solid composition.

2. The process of claim 1 conducted in the presence of an aliphatic alcohol.

3. The process of claim 2 conducted in the additional presence of phenol or a halo-, $C_{1-4}$alkyl- or di($C_{1-4}$alkyl) amido-substituted phenol.

4. The process of claim 1 wherein the inert reaction diluent is a hydrocarbon or halohydrocarbon.

5. The process of claim 1 wherein the reaction is conducted at a temperature from 50° C. to 120° C.

6. The process of claim 1 wherein the halide compound is $TiCl_4$.

7. The process of claim 1 wherein the metal M is Mg.

8. The process of claim 1 wherein the metal T is Ti, Zr, or a mixture of Ti and Zr.

* * * * *